(12) United States Patent
Metcalf et al.

(10) Patent No.: US 12,000,816 B2
(45) Date of Patent: Jun. 4, 2024

(54) SYSTEM AND METHOD OF SENSING AND PROCESSING MULTIVARIATE PRINTING PROCESS DATA

(71) Applicant: Baldwin Technology Company, Inc., St. Louis, MO (US)

(72) Inventors: Stephen J. Metcalf, Hudson, WI (US); Jacob Schwertel, Minneapolis, MN (US); Riley Swanson, River Falls, WI (US); Pete Bremer, River Falls, WI (US); Jared Wertz, River Falls, WI (US)

(73) Assignee: Baldwin Technology Company, Inc., St. Louis, MO (US)

( * ) Notice: Subject to any disclaimer, the term of this patent is extended or adjusted under 35 U.S.C. 154(b) by 516 days.

(21) Appl. No.: 17/030,143

(22) Filed: Sep. 23, 2020

(65) Prior Publication Data
US 2021/0088490 A1  Mar. 25, 2021

Related U.S. Application Data

(60) Provisional application No. 62/904,663, filed on Sep. 23, 2019.

(51) Int. Cl.
| | |
|---|---|
| *G01N 33/00* | (2006.01) |
| *B41F 33/02* | (2006.01) |
| *B41M 7/00* | (2006.01) |
| *B41M 99/00* | (2006.01) |

(52) U.S. Cl.
CPC ......... *G01N 33/0047* (2013.01); *B41F 33/02* (2013.01); *B41M 7/0081* (2013.01); *B41M 99/00* (2013.01); *G01N 33/0009* (2013.01)

(58) Field of Classification Search
CPC .......... G01N 33/0047; G01N 33/0009; B41M 7/0081; B41M 99/00
See application file for complete search history.

(56) References Cited

U.S. PATENT DOCUMENTS

| | | | |
|---|---|---|---|
| 4,928,112 A | 5/1990 | Hock et al. | |
| 8,641,236 B2 | 2/2014 | Martinez et al. | |
| 10,419,644 B2 | 9/2019 | Xu et al. | |
| 2007/0106962 A1* | 5/2007 | Sakakibara | ............ H04N 1/58 |
| | | | 716/100 |
| 2010/0192792 A1 | 8/2010 | Hall et al. | |

(Continued)

FOREIGN PATENT DOCUMENTS

CA  2235880 A1 * 11/1998 ............ G01N 33/48

OTHER PUBLICATIONS

The International Search Report and Written Opinion rendered by the International Searching Authority for PCT/US20/52300, dated Dec. 17, 2020, 8 pages.

*Primary Examiner* — Benjamin R Schmitt
(74) *Attorney, Agent, or Firm* — Skaar Ulbrich Macari, P.A.

(57) ABSTRACT

A system and method of receiving and processing granular printing and curing data, and graphically displaying data to improve quality and production. The outputted data can include graphical information illustrating relationships between important multivariate data in a typical industrial printing or converting process. One or more chemical sensors can measure curing data and communicate the data for processing and control of the subject machines of the system.

6 Claims, 9 Drawing Sheets

(56) References Cited

U.S. PATENT DOCUMENTS

| | | | |
|---|---|---|---|
| 2015/0253165 A1* | 9/2015 | Ajay | ................... G01F 1/66 |
| | | | 73/28.01 |
| 2017/0073445 A1 | 3/2017 | Hiraoka | |
| 2018/0154657 A1 | 6/2018 | Iio et al. | |
| 2018/0281302 A1 | 10/2018 | Condello et al. | |

* cited by examiner

SYSTEM AND METHOD OF SENSING AND PROCESSING MULTIVARIATE PRINTING PROCESS DATA

PRIORITY

This application claims priority to and the benefit of U.S. Provisional Patent Application No. 62/904,663, filed Sep. 23, 2019, which is fully incorporated herein by reference.

FIELD

The present invention relates generally to printing and curing systems and, more particularly, to systems configured to receive, process, and output multivariate data related to industrial printing or converting processes.

BACKGROUND

Industrial and commercial printing presses are high-throughput, high-precision machines. Each color of ink used on a printing press has its own dedicated set of rollers and cylinders to distribute and apply the ink to the substrate. High intensity light emitting diode (LED) systems are often used in curing systems to emit the radiation in the wavelengths required, e.g., ultraviolet light, to cure the ink during the printing process. The curing systems can be installed at various places on the printing press.

Applied inks and coatings are cured at rapid rates with the use of these high intensity LED systems. Moreover, manual inspection is needed to inform the curing system operator of necessary adjustments to the curing equipment to provide the best quality output. This process currently requires extensive human interaction, which can lead to waste and less effective or optimal production.

Currently, a printing press operator must perform a number of manual tests and inspection steps throughout the printing process to monitor and adjust various printing parameters, including for example, curing system power levels, ink application volumes and print speeds, and the like. This is inefficient, labor intensive, and can result in poor or inconsistent quality of finished products. The sampling rate for manual inspection of printed articles, or various critical information during the printing process, is also very low. As such, an automated process with a fast sampling rate would greatly improve production efficiency and quality.

SUMMARY

The present invention provides a system and method of receiving and processing granular printing and curing data, and graphically outputting data to improve quality and production. The outputted data can include graphical information illustrating relationships between important multivariate data in a typical industrial printing or converting process. These relationships can provide actionable insights and programmable recommendations for process intervention events using what is referred to as a radar chart (also referred to as a web chart, spider chart, star chart, star plot, cobweb chart, irregular polygon, polar chart, or Kiviat diagram). Such a radar plot is a graphical method of displaying multivariate data in the form of a two-dimensional chart of a plurality of variables represented on axes starting from the same point.

Conventionally, sensor data is isolated in the way that it is collected and depicted, and as such is limited in its ability to be analyzed and inspected to improve a printing or converting process. In other words, a typical machine operator or production quality supervisor does not have a useful method of viewing such data graphically in aggregate in a way that could surface immediate insights into relationships between the multivariate data, such as when one variable changes or how it may impact a change in another variable. Current manual processes for print quality and cure level assessment prohibit the rapid and consistent sampling made possible by the automated system of the present invention. The benefits of automated cure level and print quality monitoring includes a reduction in labor requirements, reduction in under-cured production articles, a reduction in material and resource waste, etc.

In certain embodiments, one or more chemical sensors are provided and are capable of taking readings of curing levels every 250 milliseconds, in an enclosure or housing designed to provide consistency of gas flow. This rapid rate of data acquisition will produce readings that are smooth and consistent and will minimize false data from external factors. This enables the system to quickly react to variations in curing level, thereby leading to less wasted product.

Embodiments of the one or more chemical sensors employed for the present invention can include an air input port, one or more air flow channels, one or more sensors configured to measure gasses released from the cured surface (e.g., the amount of volatile organic compounds (VOCs)) at a portion of one or more of the air flow channels, a fan, and an output port. The one or more air flow channels can undulate through a cartridge housing and can include one or more turbulence generator channels having one or more extending fins to mix the incoming air with the gasses prior to measurement by the one or more sensors.

A similar system can be devised using cameras or other optical sensors to detect the level of cure on printed or coated substrates. A device that makes contact with a printed or coated substrate can also be implemented with the present invention to assess the cure level of a surface.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
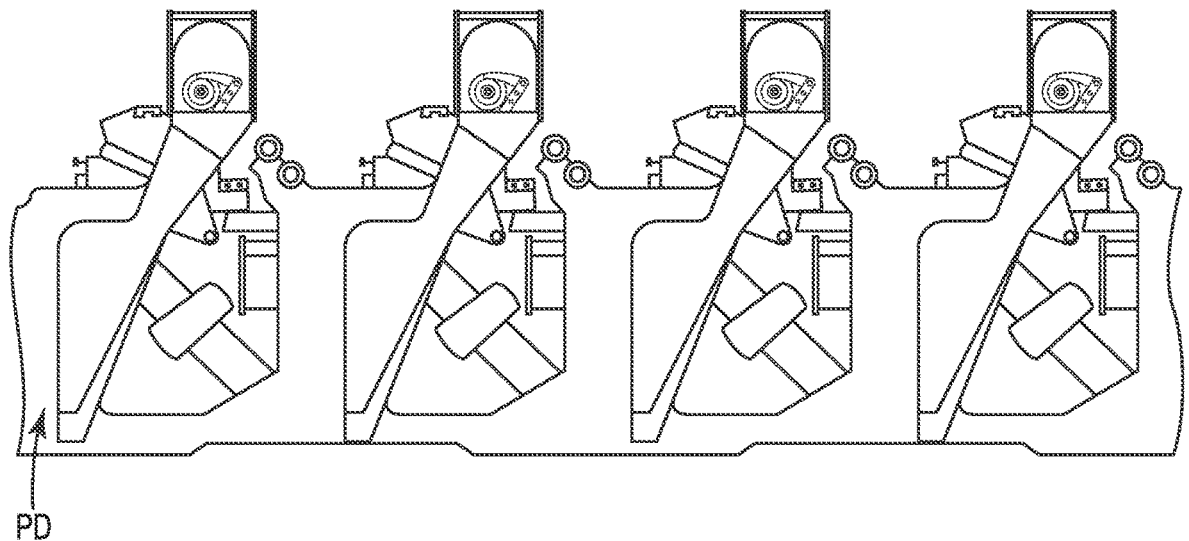
FIG. 1 shows an exemplary embodiment of an industrial printing machine for use with the system of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention.

Figure 2:
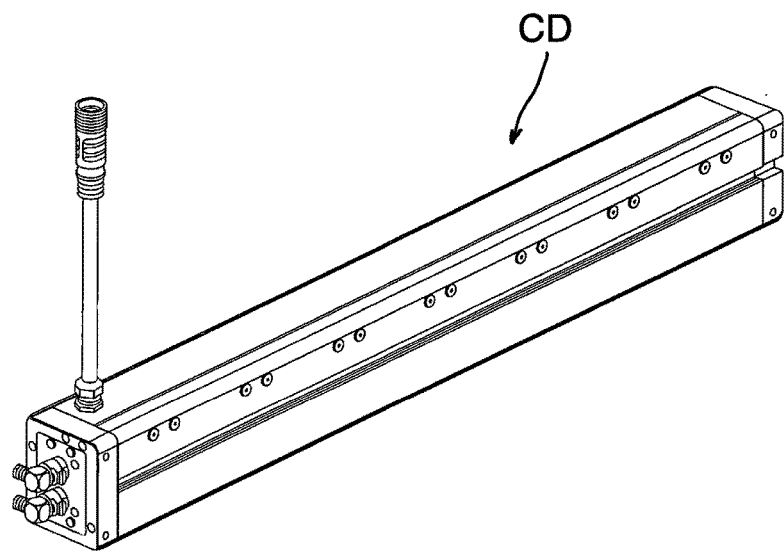
FIG. 2 shows an exemplary embodiment of an LED curing device for use with the system of the present invention.

FIGS. 1-2 depict examples of known industrial printing PD and curing CD machines or devices 102 capable of incorporating and employing the systems and methods of the present invention. These example systems and devices are provided merely for illustrative purposes and are not intended to be limiting. The present system is capable of use with current and future printing and curing devices in the field where data, e.g., information from sensors, is received and used to facilitate production. U.S. Pat. No. 8,641,236 and U.S. Patent Pub. No. 2017/0102138 A1 disclose exemplary LED curing systems, each of which is fully incorporated herein by reference.

Referring to FIGS. 3-15, the present invention provides a system and method of receiving and processing granular printing and curing data from sensors, and graphically outputting data to improve quality and production. The outputted data can include graphical information illustrating relationships between important multivariate data in a typical industrial printing or converting process. These relationships can provide actionable insights and programmable recommendations for process intervention events using what is referred to as a radar chart (also referred to as a web chart, spider chart, star chart, star plot, cobweb chart, irregular polygon, polar chart, or Kiviat diagram). Such a radar plot is a graphical method of displaying multivariate data in the form of a two-dimensional chart with multiple quantitative variables represented on axes starting from the same point. Other charts or graphical outputs of the multivariate data are envisioned as well for the present invention.

Figure 3A:
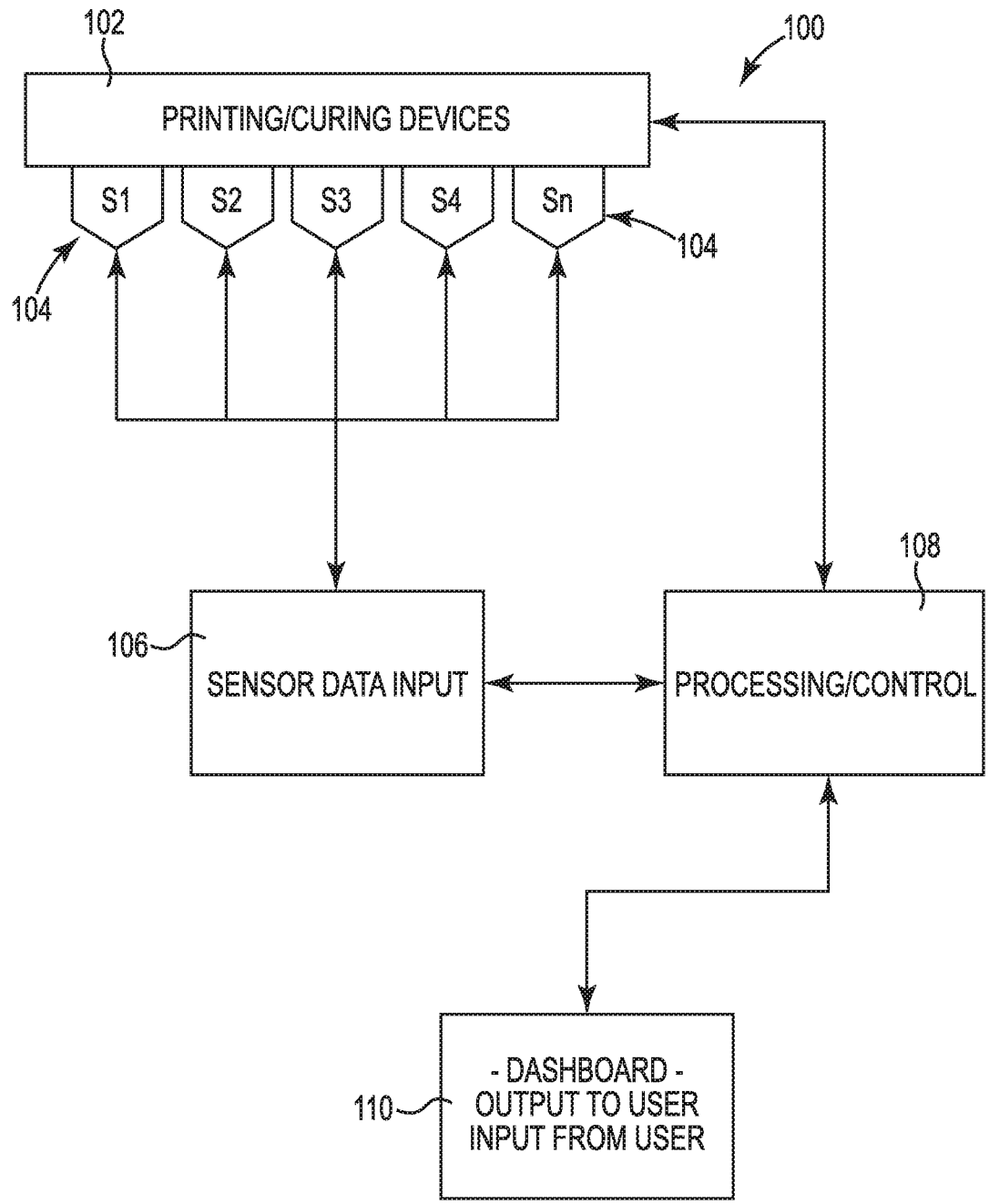
FIG. 3a is a diagram of a system of sensing and processing multivariate data for printing processes, in accordance with embodiments of the present invention.
Figure 3B:
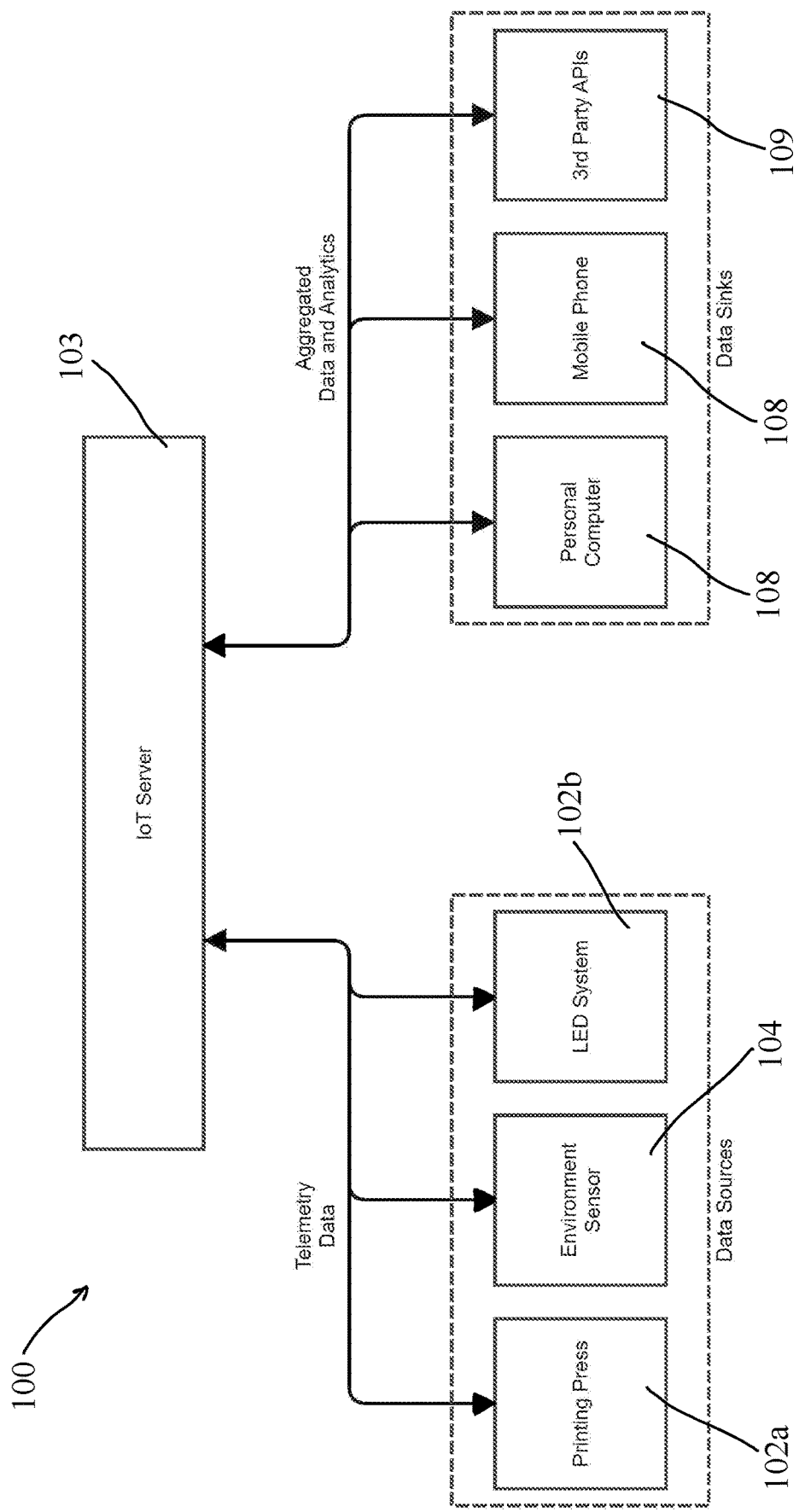
FIG. 3b is a diagram of a system of sensing and processing multivariate data for printing processes, including telemetry data, IoT servers, and aggregate data and analytics processing at computing devices, in accordance with embodiments of the present invention.

As shown in FIGS. 3a-3b, the system 100 of the present invention can include one or more machines 102, such as printing machines or presses 102a (e.g., industrial sheetfed printing, flexographic printing, etc.) and curing devices 102b (e.g., high intensity LED devices), one or more sensors 104 (e.g., S1 . . . Sn), and one or more computing devices 108. The sensors 104 are in operative communication with the computing device 108 via one or more data or communication channels. Data from the sensors 104 is received, aggregated, and processed at the one or more cloud-based servers 103 and/or the computing devices 108. The data can be inputted through a sensor data input 106 and presented at a user control display or dashboard 110. In various other embodiments, the sensors 104 can be in operative communication with control or computing devices to receive and process data, without implementation of the software dashboard 110 features disclosed herein.

The devices and systems running the software of the present invention can include one or more computing devices 108, including local desktop or portable computing devices, handheld or mobile devices (e.g., smartphones, tablets, etc.), and networked cloud-based server systems 103. APIs 109 can be provided to further facilitate use of the system 100 and integration and interaction with the software to monitor and control the machines or devices 102, the printing process, etc.

Referring to FIG. 3b, in various embodiments, the cloud-based server 103 can collect, aggregate, store, and/or perform processing on the received data from the data sources (machines 102, sensors 104, etc.) and distribute the aggregated data and analytics for use, displaying, and further processing by the one or more computing devices 108. The system 100 can utilize "Internet of Things" (IoT) technology, including the cloud-based servers 103, to collect the multivariate data through the electronic and mechanical sensors 104 and equipment installed at various points in the production process (e.g., edge devices). Data collected from these edge devices is typically collected at high frequencies (per second or millisecond) and is telemetered into a database (e.g., IoT server 103) where it is persisted with time stamps and relative descriptive elements. The multivariate data described herein and collected in such a manner is immediately available for processing and/or displaying at a radar chart of the user dashboard 110 (e.g., at computing devices 108). The dashboard 110 interface is programmed and configured to provide a plurality of visual representations of the sensed data from the edge devices, and can receive user inputs or selections to further alter or customize the displaying of data and to control the operation of the printing and curing machines or devices 102.

The data surfaced, processed, and presented via the systems and methods of the present invention integrates multivariate data from the sensors 104, established at key points in an industrial printing process. This sensor data can be obtained from a myriad of sensing and monitoring devices and can include: color measurement (Delta E, Hue, etc.), ink (density or thickness, viscosity, temperature, etc.), ultraviolet ("UV") curing (curing apparatus performance and power level, as well as age and condition of wearable elements), corona surface treatment (data including apparatus performance and power level, as well as age and condition of wearable elements), inspection (image defect detection, visual inspection of physical elements of the machine, such as die-cutting depth and registration, gas emission, UV curing inspection via sensors to detect a relative level of cured inks, coatings, adhesives, etc.), process machinery (including the speed of the printing press or converting line, and/or information related to its mechanical components, such as the pressure and temperature of rollers, its vibration level, and other data related to its performance), image color registration (data depicting the degree of unit-to-unit registration of colors from multiple printing units), cooling (data from auxiliary air or process water cooling systems, such as temperature, flow rates, and water quality when applicable), ambient environment (data from the production facility, including ambient temperature, humidity, airborne contamination, etc.), and external environmental information (including weather data, barometric pressure, outdoor air quality, etc.).

The system 100 facilitates the inspection of the printing process data as it relates to an individual printing unit 102 and the curing process and the color or chemistry/coating being printed (e.g., cyan, magenta, yellow, black, white, clear varnish/coating, adhesive, etc.). The system 100 can also display multivariate data to be depicted in aggregate for all printing stations, devices, and units on the machine 102.

Figures 4A, 4B:
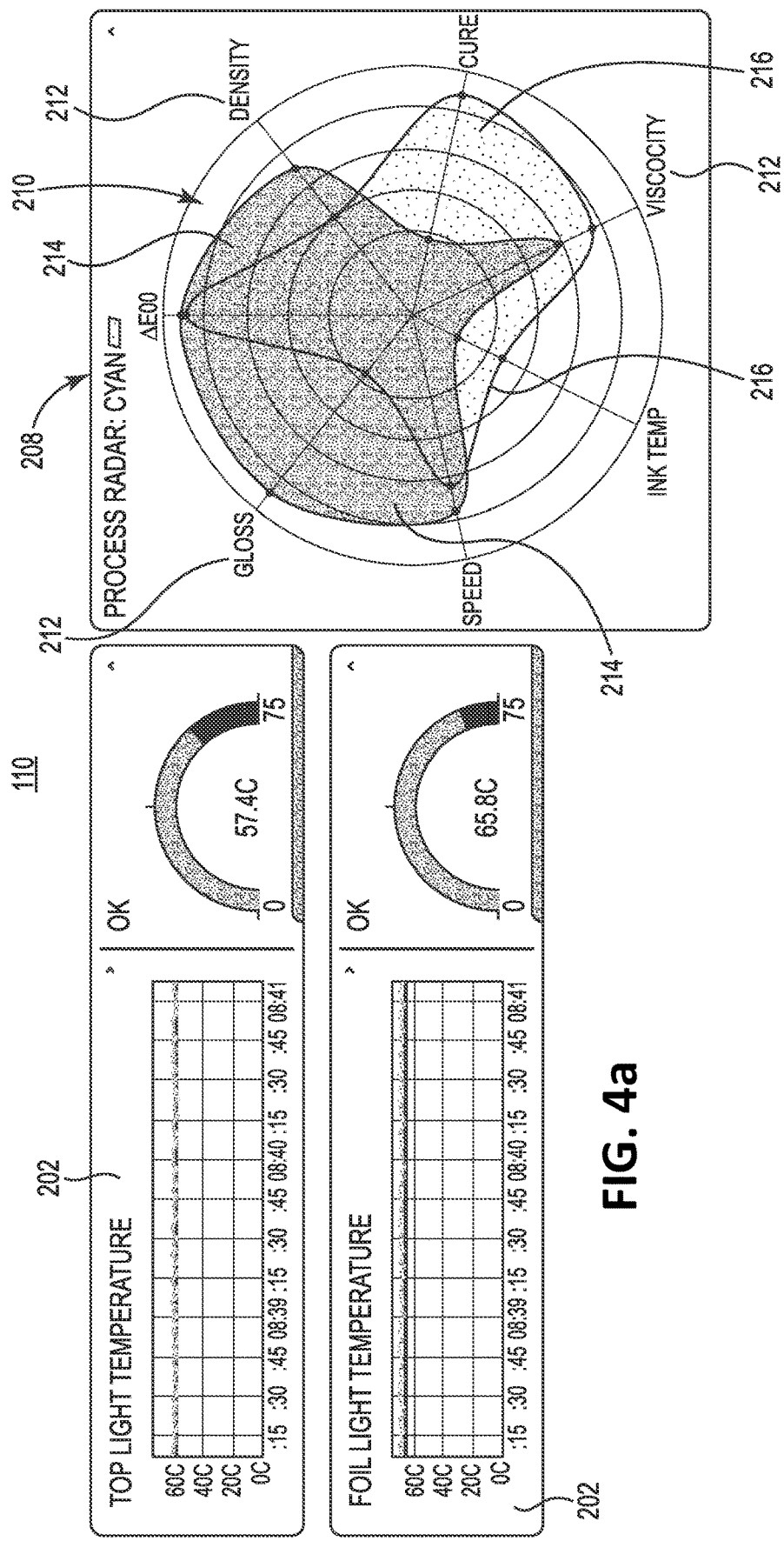
FIGS. 4a-4c show regions of a displayed user dashboard interface for use with a system of sensing and processing multivariate data for printing processes, in accordance with embodiments of the present invention.
Figure 4C:
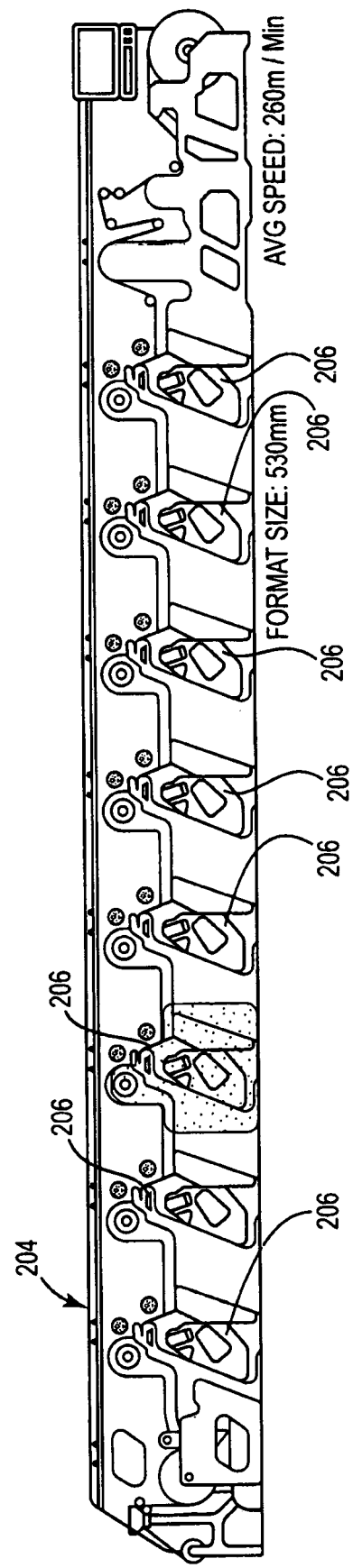
Figure 5:
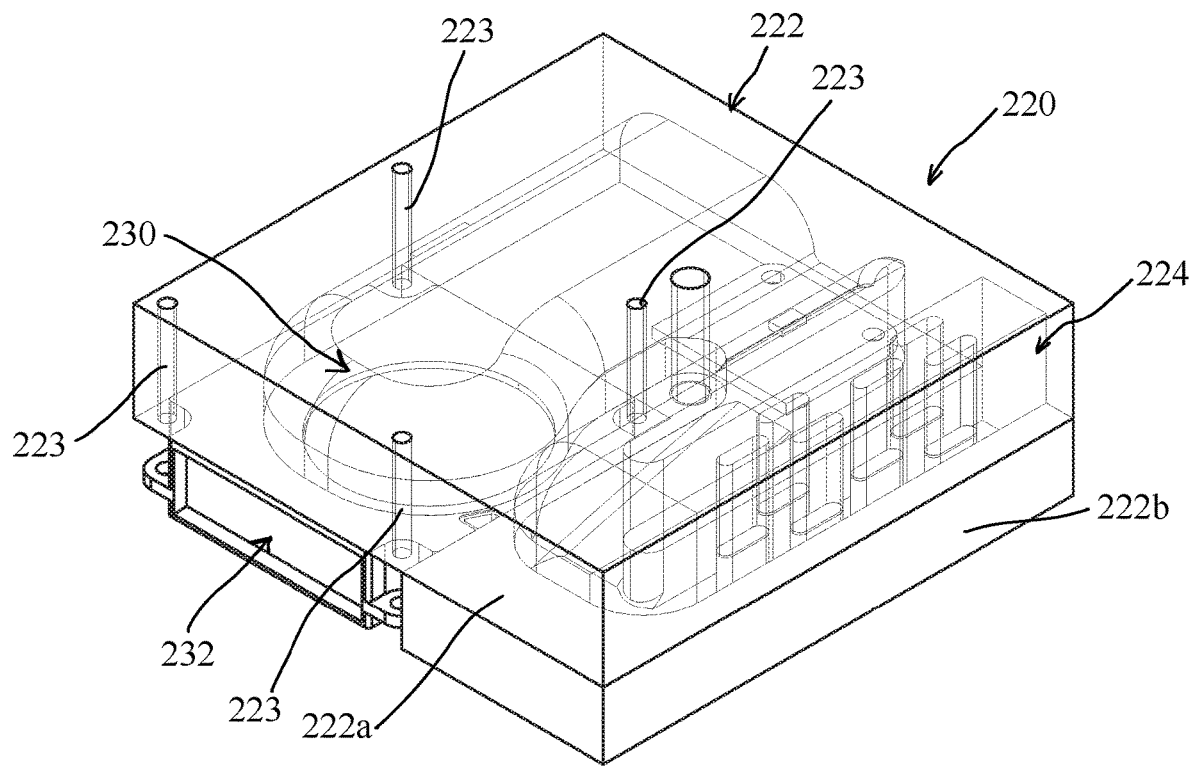
FIG. 5 shows a partially transparent perspective view of a sensor cartridge for use with a system of sensing chemical gas emissions during printing processes, in accordance with embodiments of the present invention.
Figure 6:
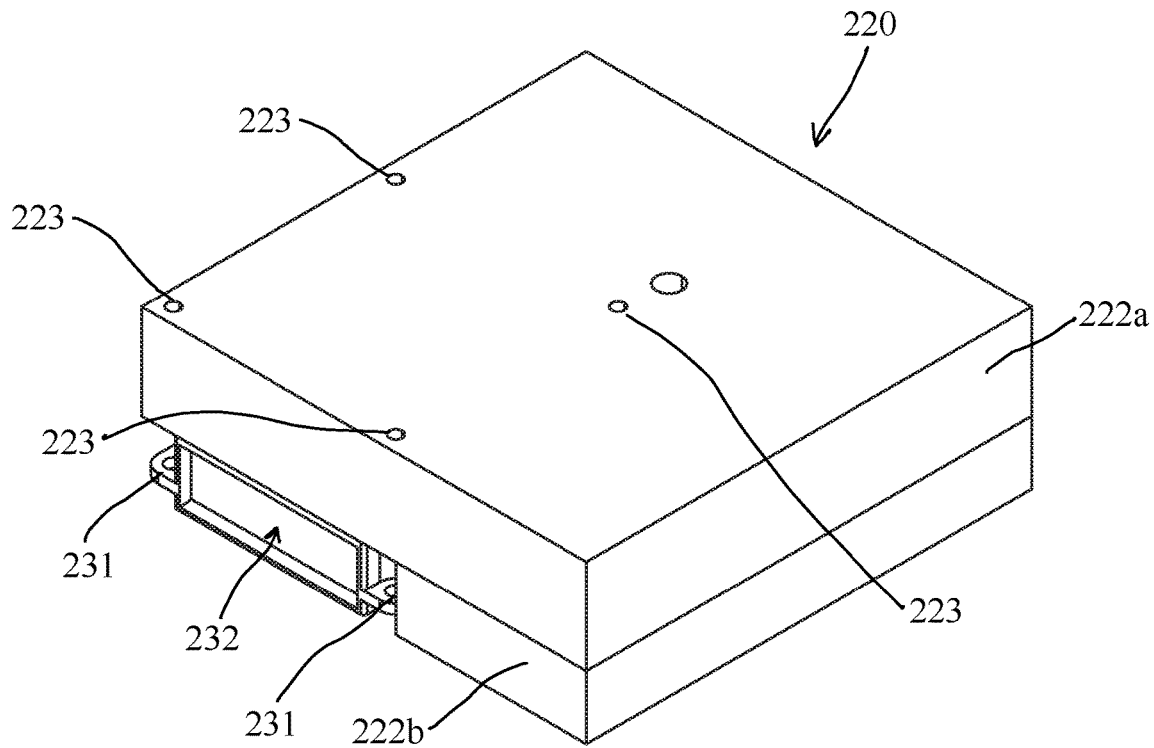
FIG. 6 shows a perspective view of the sensor cartridge of FIG. 5 for use with a system of sensing chemical gas emissions during printing processes, in accordance with embodiments of the present invention.

Referring to FIGS. 4a-4c, the user dashboard 110 can present a wealth of information received from the sensors 104 of the devices 102, in a graphical and/or textual output format on the one or more computing devices 108. Various windows or display regions 202 can be provided to display the information received and processed from the sensors 104, as shown in FIG. 4a. Further, as depicted, a graphical representation of the printing machine 204 is displayed and can include selectable images of the individual units 206 included with the machine 204, as demonstrated in FIG. 4c. As such, the user operator can select a particular unit 206 of interest and the system 100 will correspondingly display the data and information for that unit 206. Units can be compared against other units, or isolated for specific unit analysis.

As shown in FIG. 4b, the radar chart (e.g., process radar) region 208 of the outputted dashboard display 110 can include plotting for multiple data points 212 from the selected unit 206 (e.g., FIG. 4c) to monitor for defects, color inspection, ink curing information, and other relevant conditions and operations. This processed and displayed data can include values for Delta E, density, cure, viscosity, ink temperature, speed, gloss, gas emission, or any of the sensor data described herein. The specific data received and displayed in the exemplary dashboard 110 and radar plot 208 of FIGS. 4a-4c is merely illustrative and is not intended to be limiting. The various information displays and interface regions (interactive and non-interactive) of FIGS. 4a-4c can be displayed separately, combined on one display or screen region, or a combination thereof.

The user can select and deselect multivariate data channels (e.g., data from sensors) for inspection and display via the radar chart 208. Depiction of a live or current view 214 of the collected data is fed from the machine 102 (e.g., directly or via the IoT servers 103) in the form of a first visual plot between axes. A historical time point is user selectable for the same multivariate data in a second visual plot 216 which can be highlighted with a different color or highlighting method to present the differences between the historic point and the live view. An average of the same multivariate data can be presented in a third plot using a different color or highlighting method to highlight differences between the live view, the historical view, and the average view. The selection of data used for the average plot can be selected and constrained by the user in terms of its time (e.g., all-time, annual average, monthly average, average by a production job, average over the last hour, etc.).

Data plotted in the radar chart 208 can allow visual sub-inspection into live and historical data values by allowing the user to select an individual axis or select multiple axes for comparison of selected data variables. Such outputted data can be downloaded or extracted into other useful forms, such as those adapted for feeding external spreadsheets (e.g., .CSV files), databases, and the like.

Indicia or alerts in the radar chart 208 or other display regions can visually indicate areas of concern, where data relationships are detected that may indicate concern. For example, if the speed of the machine 102 causes other data to exceed target tolerances set by the user in advance, a visual indication of this area of concern would be displayed on the chart 208 in the form of another color, a flashing data or graphical element, a pop-up notification, or the like. As another example, if the sensed curing or gas emission data indicates problems with the speed, dwell, or control of the ink curing process, visual indicia of this issue can be displayed as well. These are just illustrative examples of the various visual alerts and display highlighting methods that can be employed by the system 100. Visual displays and indications can be implemented to address any of the processed and displayed information or data detailed herein.

Intervention events resulting from received data relationships can be processed by the system 100 and presented to the end user in the form of suggested ways to improve the process and bring multivariate data variables back within their target tolerances. For example, "reduce the machine speed below 200 m/min in order to bring curing to within target thresholds," or "increase UV curing output power because roller temperature has dropped below target thresholds," "slow machine speed because gas emission indicates ink curing is not within desired target," and like messages can be displayed or otherwise presented to the user for action.

The system 100 and its software, e.g., running on one or more computing devices 108 and/or the one or more IoT servers 103, can be programmed such that various information and recommendations can be processed to signal and control the operatively connected machines 102 (e.g., printing press systems, curing systems, etc.) to automatically make adjustments where possible via presentation of an "automatically optimize," or similar selection. As such, the user can allow the data intelligence from the process radar 208 and the computing power of the system 100 to make adjustments to the operating parameters of the machines 102 that alter the measured values (such as those listed herein above) in accordance with system recommendations (e.g., press speed, temperature, power, cure, etc.).

Referring to FIGS. 5-10, an embodiment of the one or more sensors 104 can include one or more chemical or cure sensors 220. The one or more sensors 220 are placed near the curing or cured surface monitored by a curing system control mechanism and is tuned to make frequent samples of gasses released from the surface. As a result, the sensor 220 can automate the cure consistency verification process. The chemical sensor 220 can include a cartridge housing 222 configured to house or define an air input port 224, one or more air flow channels 226, one or more sensor devices 228, one or more fans 230 (e.g., variable fans), and an output port 232. The one or more air flow channels 226 can undulate through or otherwise be defined in the cartridge housing 222 and can include one or more turbulence generator channels 234 having one or more extending fins 236 to mix the incoming air with the emitted gasses prior to measurement by the one or more sensor devices 228.

The cartridge housing 222 can include a first half or portion 222a and a second half or portion 222b. The portions 222a, 222b can be separate, integrated or formed as one unit, or otherwise manufactured to create the various channels, ports, fins, etc. The housing 222 can include a plurality of fastening apertures 230 provided to receive fasteners to facilitate mounting of components, housing sections, and the like. The housing 222, e.g., the second portion 22b, can further include mounting apertures 231 that align with corresponding apertures 230 to facilitate mounting components, the fan 230 device, etc. The cartridge housing 222 can include a connector mechanism 240 that enables selective insertion and removal into and out of the machine 102. As such, the housing 222 and its corresponding components can be easily replaced, e.g., as the result of a failed or defective sensor 228, fan 230, etc.

Figure 7:
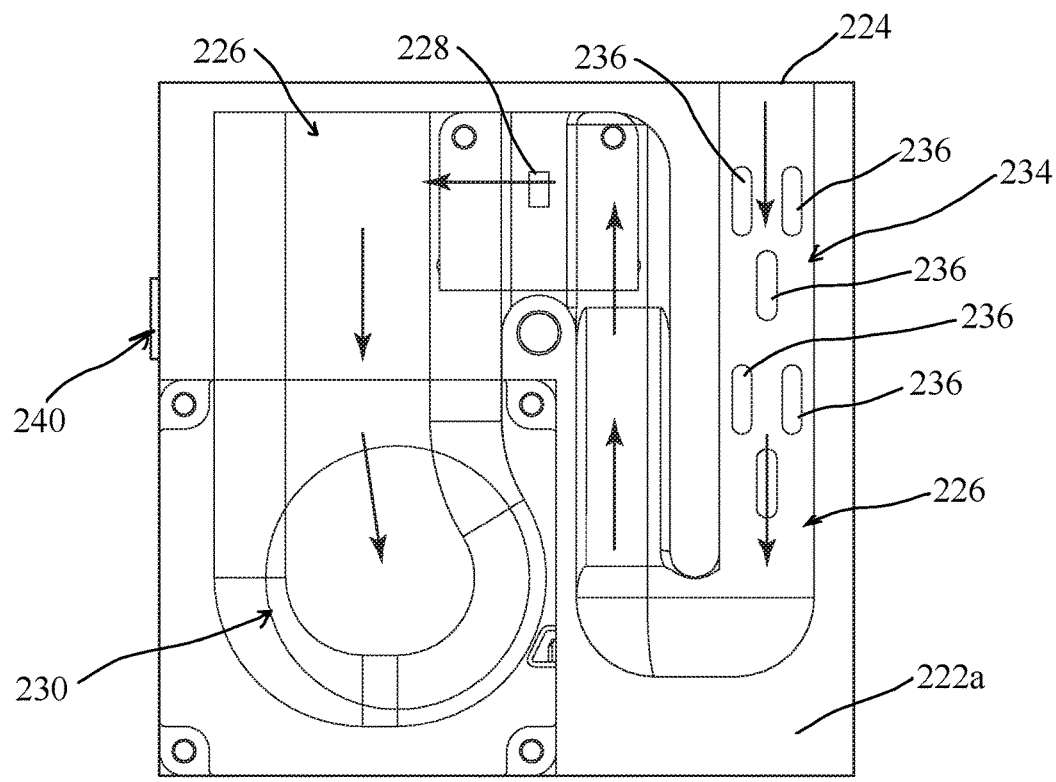
FIG. 7 shows a top view of a first portion or half of the sensor cartridge of FIG. 5 for use with a system of sensing chemical gas emissions during printing processes, including air flow through air flow channels, in accordance with embodiments of the present invention.
Figure 8:
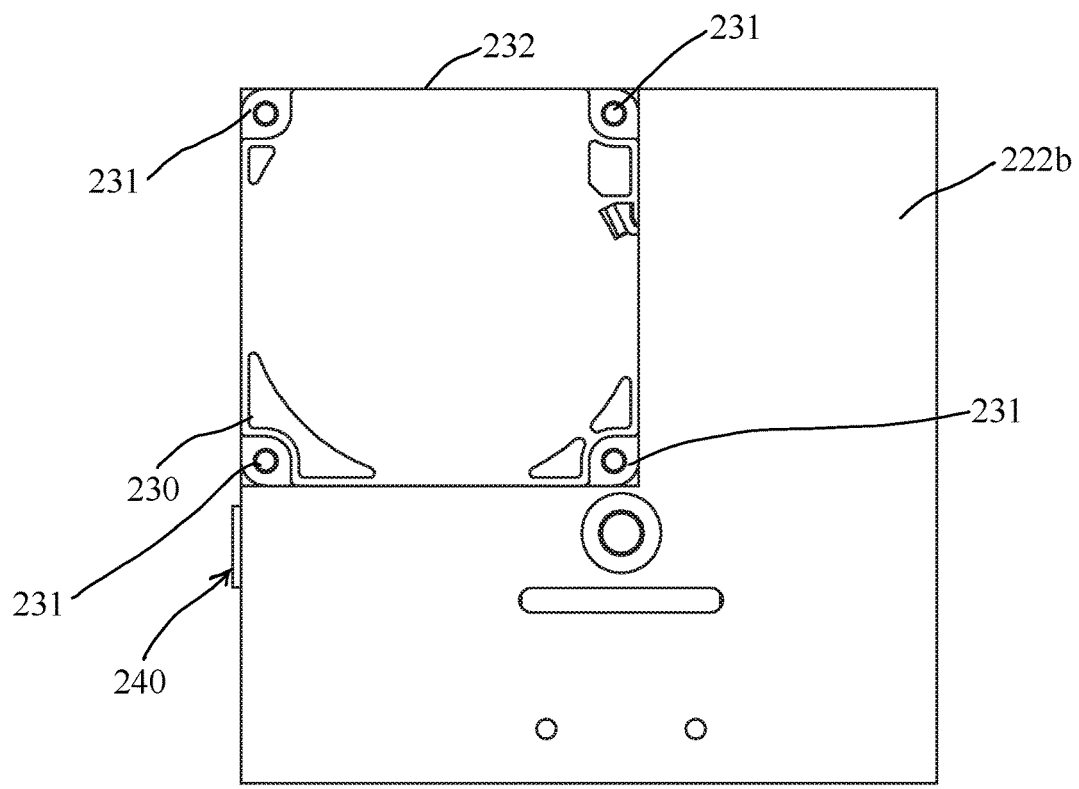
FIG. 8 shows a top view of a second portion or half of the sensor cartridge of FIG. 5 for use with a system of sensing chemical gas emissions during printing processes, in accordance with embodiments of the present invention.
Figure 9:
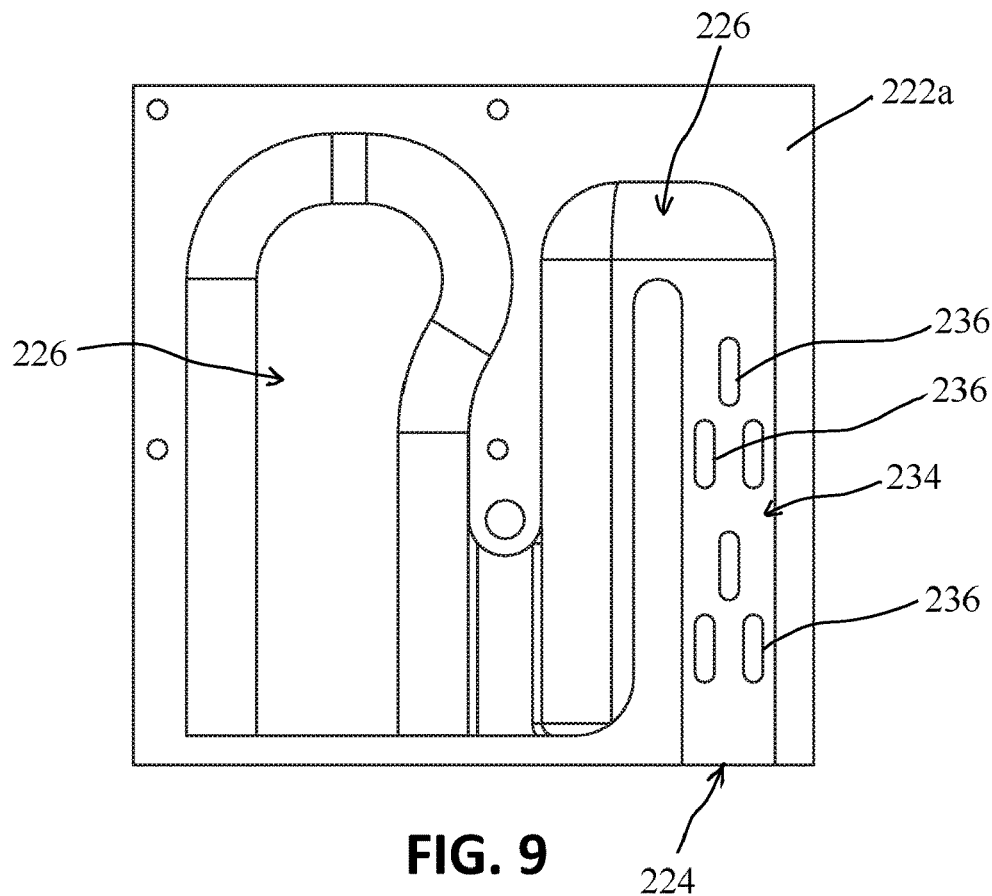
FIG. 9 shows a top view of the first portion or half of the sensor cartridge of FIG. 5 for use with a system of sensing chemical gas emissions during printing processes, in accordance with embodiments of the present invention.
Figure 10:
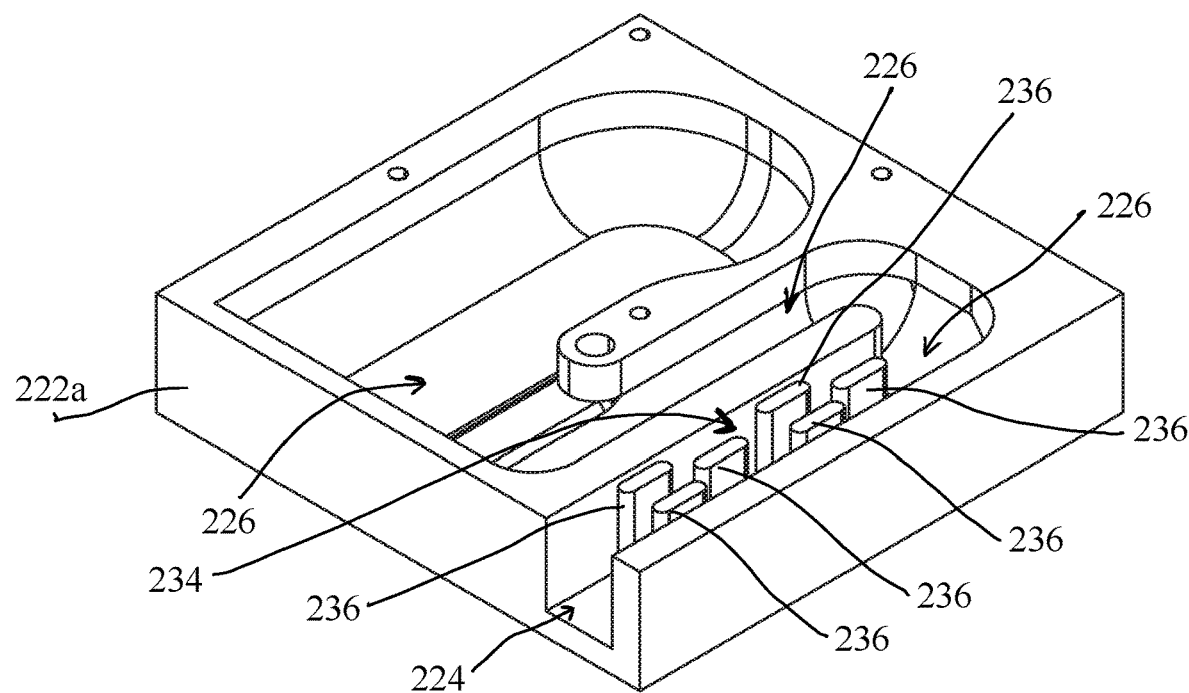
FIG. 10 shows a perspective view of the first portion or half of the sensor cartridge of FIG. 5 for use with a system of sensing chemical gas emissions during printing processes, in accordance with embodiments of the present invention.
Figure 14:
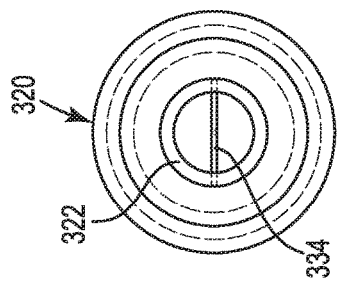
FIGS. 11-15 show a duct-type chemical sensor for use with a system of sensing chemical gas emissions during printing processes, in accordance with embodiments of the present invention.
Figure 15:
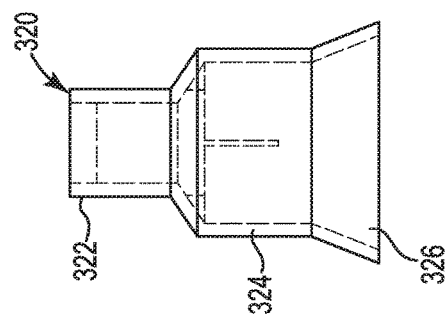
Figure 12:
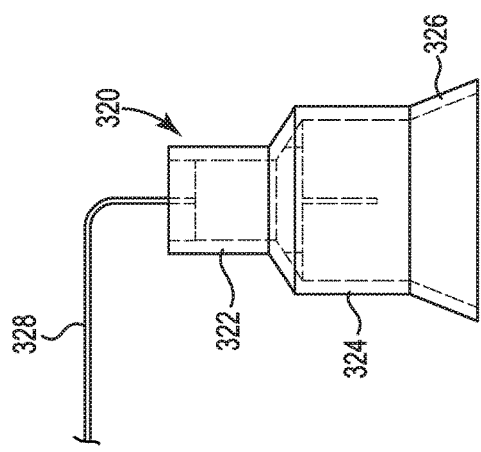
Figure 13:
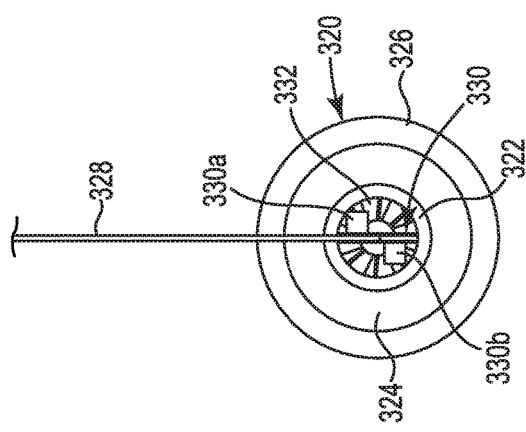
Figure 11:
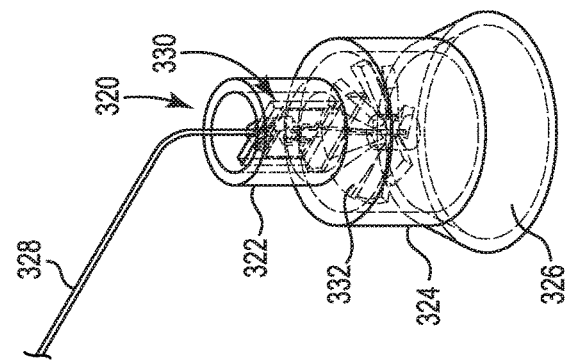

The sensor device 228 is adapted to measure gasses released from the cured surface, e.g., the amount of volatile organic compounds (VOCs), at a portion of the one or more air flow channels 226. The sensor 220 monitors the curing or cured surface and is tuned to make frequent samples of gasses released from the surface. For example, the printing process involves laying ink down on a substrate (e.g., paper). As the ink cures it can give off gasses, such as VOCs. The sensor device 228 measures the exact levels of the emitted VOCs during this curing process. First, the air input port 224 takes in air off of the substrate as it passes by the sensor cartridge 222, with the fan 230 pulling air in and through the one or more air flow channels 226. The air is then pulled through the turbulence generator channel 234 and the corresponding extending fins 236, which causes turbulences in the air and evenly mixes the VOCs with the air. The mixture of the incoming air and the VOCs travels to the sensor device 228 where the amount of VOCs is read or measured. After the sensor device 228 reads the amount of VOCs, the air mixture is exhausted out through the output port 232 by the fan 230. FIG. 7 includes arrows illustrating exemplary air flow through the housing 222.

In various embodiments, the chemical sensor 220 (e.g., electrochemical) is configured to detect VOCs, components of the solvent, or other applicable chemical traces related to the chemistry of the ink or coating being applied. A cured ink or coating would have a specific detectable chemical profile of vapor at known concentrations. When the concentrations deviate from predetermined desired values, the sensor provides feedback to the system 100 and alerts the operator, or automatically adjusts the curing system to compensate for the change in curing level (e.g., speed, dwell time, LED power, etc.).

Again, as detailed herein, the sensor 220 operatively communicates this data to the one or more server systems 103 and/or computing devices 108 for aggregation, processing and displaying data charts, indicia, and like information. For example, the sensor data can be displayed at the user interface regions detailed for FIGS. 4a-4c, including the display and interactive regions 202, 208.

As shown in FIGS. 11-15, one or more system sensors 104 can comprise an exemplary chemical sensor duct 320 placed near the cured surface that is monitored by a curing system control mechanism and is tuned to make frequent samples of gasses released from the cured surface. As a result, the sensor 320, like the sensor 220, can automate the cure consistency verification process. The sensor 320 is housed in a duct that controls the flow of gas being sampled from the surface of the printed or coated substrate. In certain embodiments of the sensor 320, the amount of VOCs emitted during ink curing is measured.

In various embodiments, the chemical sensor 320 is generally bell-shaped and includes a top portion 322, a central portion 324, and a base or flared portion 326. A sensor assembly 330 is mountable within the top portion 322 via mounting element 334, and one or more data channels 328 provide operative communication between the sensor 320 and the computing devices 108 and/or the server systems 103 of the system 100. In certain embodiments, the sensor assembly 330 can include an individual chemical sensor 330a and an air flow sensor 330b. A variable fan device 332 is housed below the sensor 320, e.g., within the central portion 324. The variable fan 332 ensures a constant air flow over the chemical sensor 330. For instance, a moving substrate will cause an increase in air flow entering the duct via the base portion 326 and the variable fan 332 will automatically adjust to maintain a stable and even flow over the sensor 330a.

Accordingly, changes in the composition of the outgassed vapor (e.g., VOCs) from an ink or coating layer applied to a substrate can be monitored for fluctuation. The electrochemical sensor 320 (e.g., via sensor 330a) is configured to detect components of the solvent, VOCs, or other applicable chemical traces related to the chemistry of the ink or coating being applied. A cured ink or coating would have a specific detectable chemical profile of vapor at known concentrations. When the concentrations deviate from predetermined desired values, the sensor provides feedback to the system 100 and alerts the operator, or automatically adjusts the curing system to compensate for the change in curing level.

Various computing devices 108, such as desktop computing devices and handheld or mobile devices (e.g., smartphones, tablets, etc.), can be included and adapted to process and carry out the aspects, computations, and algorithmic processing of the hardware and software systems and methods of the present invention. Computing systems and devices of the present invention may include a processor, which may include one or more microprocessors and/or one or more circuits, such as an application specific integrated circuit (ASIC), field-programmable gate arrays (FPGAs), etc. Further, the devices can include a network interface. The network interface is configured to enable communication with a communication network, other devices and systems, and servers, using a wired and/or wireless connection.

The computing devices may include memory, such as non-transitive, which may include one or more non-volatile storage devices and/or one or more volatile storage devices (e.g., random access memory (RAM)). In instances where the devices include a microprocessor, computer readable program code may be stored in a computer readable medium or memory, such as solid-state drives, mechanical drives, optical drives, memory devices (e.g., random access memory, flash memory), etc. The computer program or software code can be stored on a tangible, or non-transitive, machine-readable medium or memory. In some embodiments, computer readable program code is configured such that when executed by a processor, the code causes the device to perform the steps described above and herein. In other embodiments, the device is configured to perform steps described herein without the need for code.

It will be recognized by one skilled in the art that these operations, algorithms, logic, method steps, routines, sub-routines, and modules may be implemented in software, in firmware, in special purpose digital logic, and any combination thereof without deviating from the spirit and scope of the present invention as recited within the claims attached hereto.

The computing devices and server systems of the present invention disclosed herein may include an input device. The input device is configured to receive an input from either a user (e.g., admin, user, etc.) or a hardware or software component. Examples of an input device include a keyboard, mouse, microphone, touch screen and software enabling interaction with a touch screen, etc. The devices or computing devices can also include an output device. Examples of output devices include monitors, televisions, mobile device screens, tablet screens, speakers, remote screens, etc. The output device can be configured to display images, media files, text, or video, or play audio to a user through speaker output.

Server or cloud processing systems 103 for use or connected with the systems and devices of the present invention, can include one or more microprocessors, and/or one or more circuits, such as an application specific integrated circuit (ASIC), field-programmable gate arrays (FPGAs), etc. A network interface can be configured to enable communication with a communication network, using a wired and/or wireless connection, including communication with devices or computing devices disclosed herein. Memory can include one or more non-volatile storage devices and/or one or more volatile storage devices (e.g., random access memory (RAM)). In instances where the server system includes a microprocessor, computer readable program code may be stored in a computer readable medium, such as solid-state drives, mechanical drives, optical drives, memory devices (e.g., random access memory, flash memory), etc.

References to methods and steps such as inputting, entering, and the like can include manual user inputs, or direct generation and insertion/inclusion of data via software.

Additionally, while the methods described above and illustrated in the drawings are shown as a sequence of steps or processes, this was done solely for the sake of illustration. Accordingly, it is contemplated that some steps may be added, some steps may be omitted, the order of steps may be re-arranged, and some steps may be performed in parallel.

For purposes of interpreting the claims for the present invention, it is expressly intended that the provisions of Section 112, sixth paragraph of 35 U.S.C. are not to be invoked unless the specific terms "means for" or "step for" are recited in a claim.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiments described herein which equivalents are intended to be encompassed by the claims attached hereto.

What is claimed is:

1. A chemical sensor system configured to measure ink curing, comprising:
   a cartridge body having:
      an inlet port;
      one or more air flow channels in fluid communication with the inlet port and having at least one turbulence generator channel to mix incoming air with volatile organic compounds (VOCs);
      a chemical sensor provided in fluid communication with the at least one turbulence generator channel to measure VOCs levels;
      an outlet port in fluid communication with the chemical sensor and the one or more air flow channels; and
      a fan device configured to pull VOCs through the one or more air flow channels;
   at least one communication line to facilitate operative communication of sensor data from the chemical sensor to one or more cloud-based servers; and
   one or more computing devices in operative communication with one or more cloud-based servers, the one or more computing devices configured to:
      receive aggregated sensor data from the one or more cloud-based server; and
      display a visual dashboard on the one or more computing devices, the visual dashboard including at least a machine display region and a process radar region, with the machine display region having one or more selectable images and the process radar region having a plurality of data point plots based on the aggregated sensor data.

2. The system of claim 1, wherein the turbulence generator channel includes one or more fins.

3. The system of claim 2, wherein the one or more fins extend into the turbulence generator channel to cause turbulence to facilitate mixing of the incoming air with the VOCs.

4. The system of claim 1, wherein the cartridge body includes at least one connector adapted to provide selective removal of the cartridge body.

5. The system of claim 1, wherein the one or more air flow channels are undulating within the cartridge body.

6. The system of claim 1, wherein the fan device is provided proximate the outlet port to pull VOCs through the one or more air flow channels and out through the outlet port.

* * * * *